(12) United States Patent
Itoh et al.

(10) Patent No.: US 9,980,648 B2
(45) Date of Patent: May 29, 2018

(54) PROBE AND IMAGING APPARATUS FOR DIAGNOSIS

(71) Applicant: TERUMO KABUSHIKI KAISHA, Shibuya-ku (JP)

(72) Inventors: Ema Itoh, Hadano (JP); Isao Mori, Chofu (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 892 days.

(21) Appl. No.: 14/496,127

(22) Filed: Sep. 25, 2014

(65) Prior Publication Data
US 2015/0051485 A1    Feb. 19, 2015

Related U.S. Application Data

(63) Continuation of application No. PCT/JP2013/001853, filed on Mar. 19, 2013.

(30) Foreign Application Priority Data

Mar. 26, 2012 (JP) ................................ 2012-069682

(51) Int. Cl.
*A61B 8/00* (2006.01)
*A61B 5/00* (2006.01)
(Continued)

(52) U.S. Cl.
CPC ........ *A61B 5/0035* (2013.01); *A61B 1/00096* (2013.01); *A61B 5/0066* (2013.01);
(Continued)

(58) Field of Classification Search
CPC ........... A61B 8/00; A61B 8/13; A61B 5/0084; A61B 8/445; A61B 8/4461; A61B 8/4416;
(Continued)

(56) References Cited

U.S. PATENT DOCUMENTS

2007/0232892 A1    10/2007   Hirota
2010/0268087 A1    10/2010   Hirota

FOREIGN PATENT DOCUMENTS

EP    2 777 486 A2    9/2014
JP    11-56752 A      3/1999
(Continued)

OTHER PUBLICATIONS

Extended European Search Report dated Oct. 29, 2015, issued by the European Patent Office in the corresponding European Application No. 13770276.7. (9 pages).
(Continued)

*Primary Examiner* — Joel Lamprecht
(74) *Attorney, Agent, or Firm* — Buchanan Ingersoll & Rooney PC

(57) ABSTRACT

A probe includes a transmitting and receiving unit in which an ultrasonic wave transmitting and receiving unit and a light transmitting and receiving unit are arranged. The ultrasonic wave transmitting and receiving unit and the light transmitting and receiving unit are arranged along an axial direction. A distance L [mm] between a position of the ultrasonic wave transmitting and receiving unit in the axial direction and a position of the light transmitting and receiving unit in the axial direction, and the angular difference $\theta$ [degrees] between a transmit direction of an ultrasonic wave of the ultrasonic wave transmitting and receiving unit and a transmit direction of light of the light transmitting and receiving unit satisfy a relationship of $L=V/\omega \times \theta/360$ when having a rotary velocity $\omega$ [r/s] of the transmitting and receiving unit 221 and a movement velocity V [mm/s] of the transmitting and receiving unit 221 in the axial direction.

17 Claims, 10 Drawing Sheets

(51) Int. Cl.
*A61B 8/12* (2006.01)
*A61B 1/00* (2006.01)
*A61B 8/13* (2006.01)
*G01N 29/04* (2006.01)
*G01N 29/24* (2006.01)
*A61B 8/14* (2006.01)
*A61B 8/08* (2006.01)

(52) U.S. Cl.
CPC ............. *A61B 5/0084* (2013.01); *A61B 8/12* (2013.01); *A61B 8/13* (2013.01); *A61B 8/445* (2013.01); *A61B 8/4416* (2013.01); *A61B 8/4461* (2013.01); *G01N 29/043* (2013.01); *G01N 29/2418* (2013.01); *A61B 8/0891* (2013.01); *A61B 8/14* (2013.01); *A61B 8/5261* (2013.01); *G01N 2291/023* (2013.01); *G01N 2291/0289* (2013.01)

(58) Field of Classification Search
CPC ....... A61B 5/0066; A61B 8/12; A61B 8/0891; A61B 8/14; A61B 8/5261
See application file for complete search history.

(56) References Cited

FOREIGN PATENT DOCUMENTS

| | | | |
|---|---|---|---|
| JP | 2004-290548 A | 10/2004 |
| JP | 2007-268131 A | 10/2007 |
| JP | 2008-510586 A | 4/2008 |
| JP | 2009-183417 A | 8/2009 |
| JP | 2010-508973 A | 3/2010 |
| JP | 2010-246767 A | 11/2010 |
| WO | WO 2006/024015 A1 | 3/2006 |
| WO | WO 2008/057573 A2 | 5/2008 |
| WO | 2009/009802 A1 | 1/2009 |
| WO | WO 2010/077632 A2 | 7/2010 |
| WO | 2014/077870 A1 | 5/2014 |

OTHER PUBLICATIONS

Li et al., "Miniature integrated optical coherence tomography (OCT)—ultrasound (US) probe for intravascular imaging", Photonic Therapeutics and Diagnostics VII, Proc. of SPIE, Feb. 3, 2012, vol. 8207, No. 1, pp. 1-7.
International Search Report (PCT/ISA/210) dated Apr. 16, 2013, by the Japanese Patent Office as International Searching Authority for International Application No. PCT/JP2013/001853.

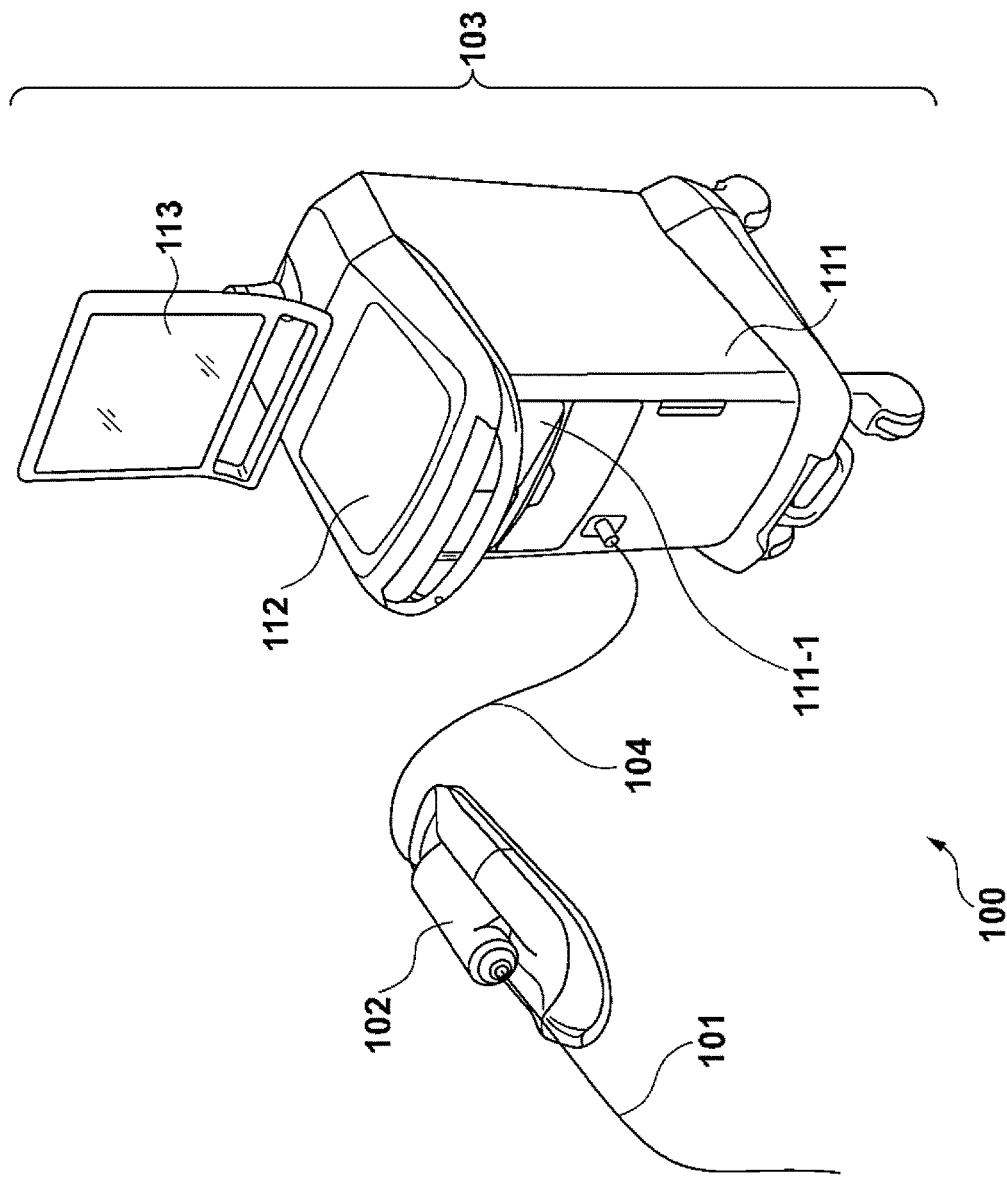
[FIG. 1]

[FIG. 2]
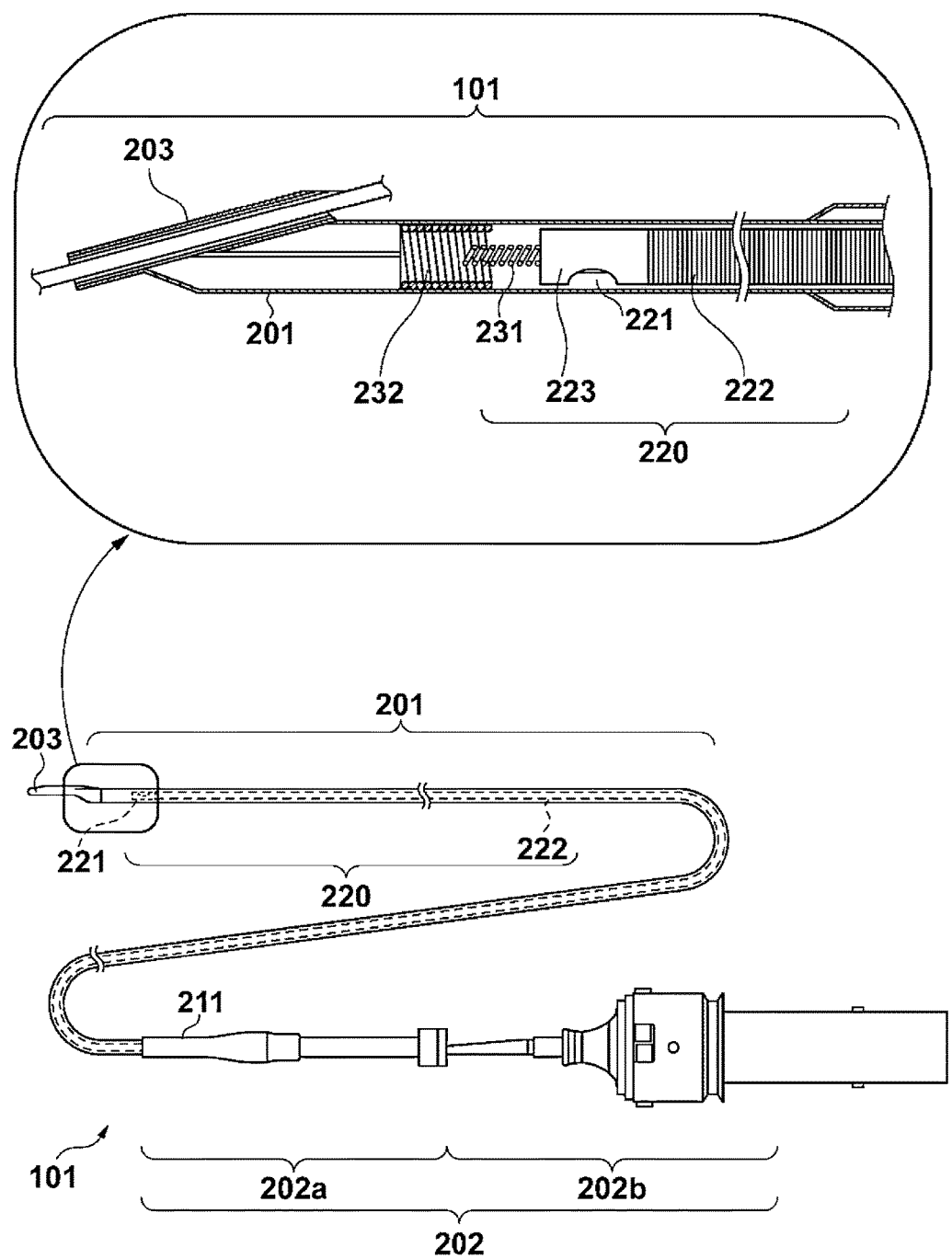

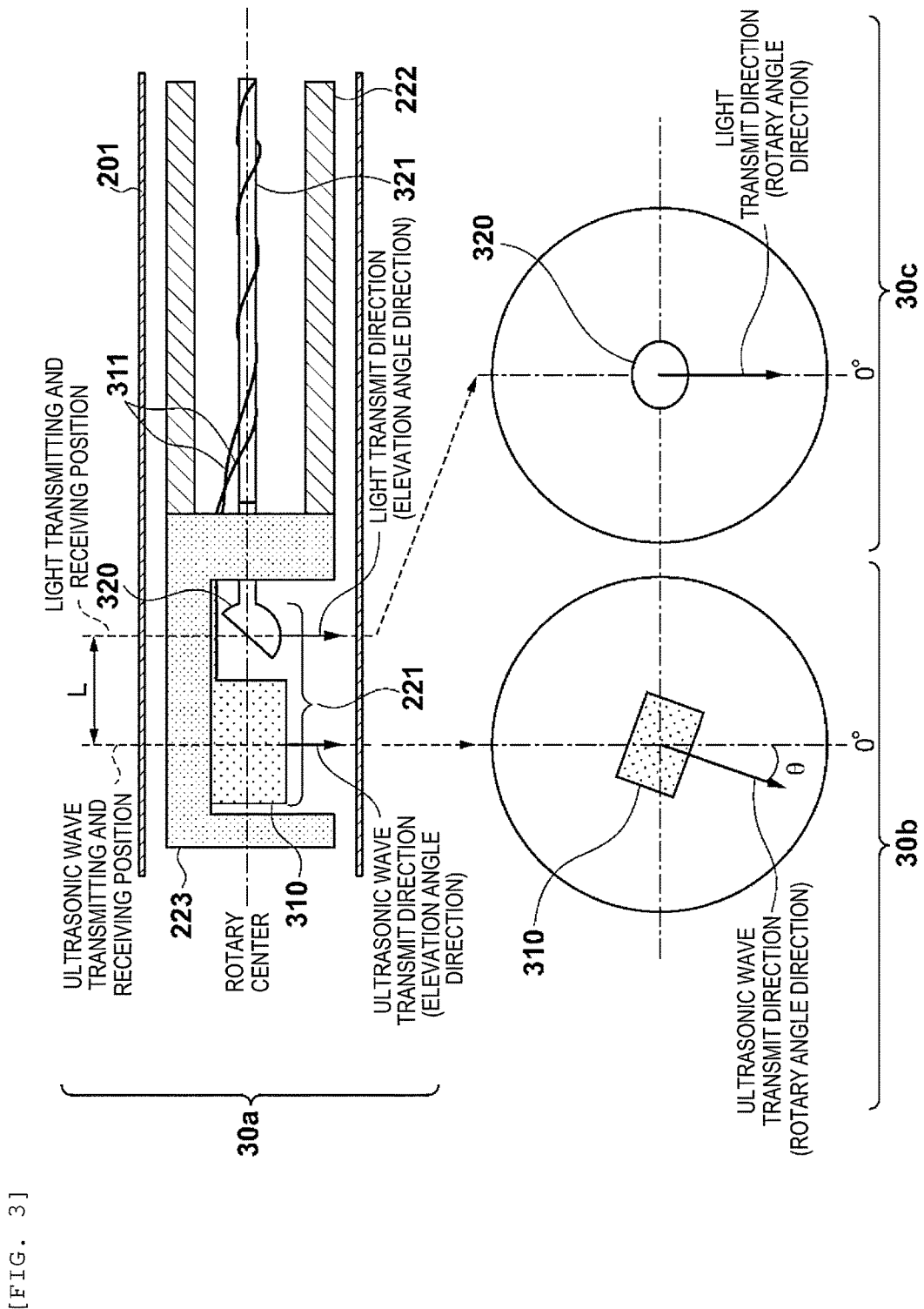
[FIG. 3]

[FIG. 4A]
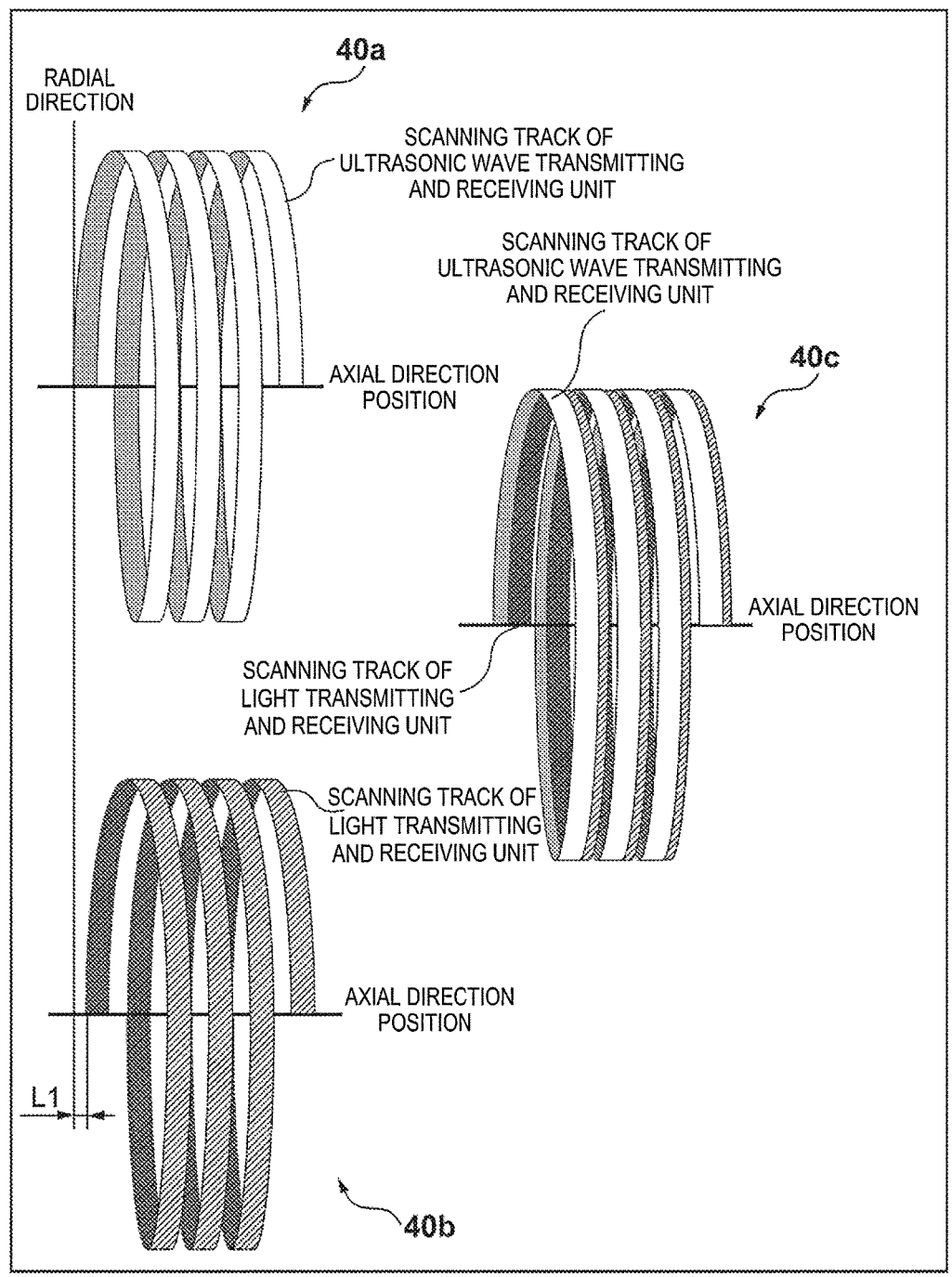

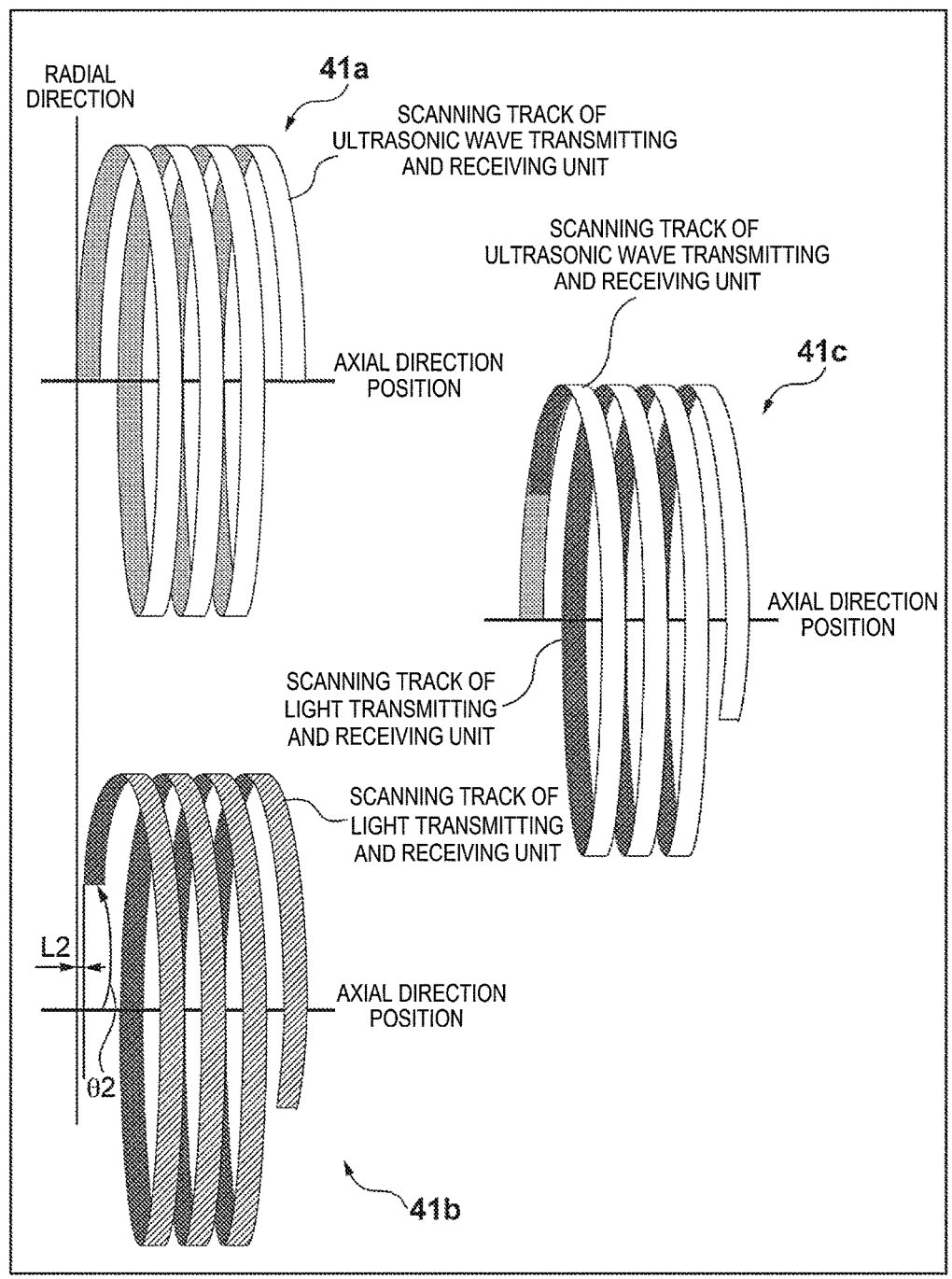
[FIG. 4B]

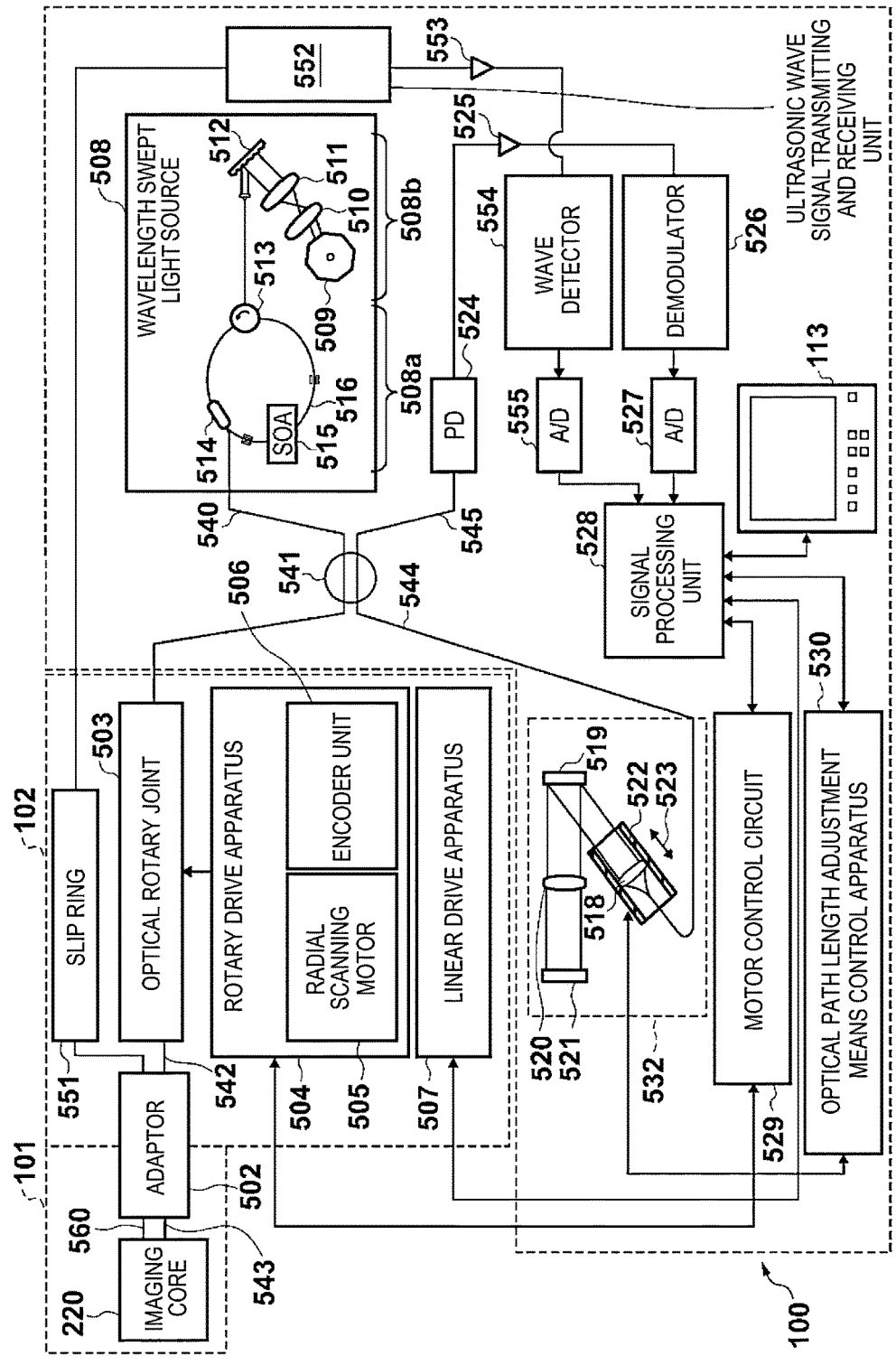
[FIG. 5]

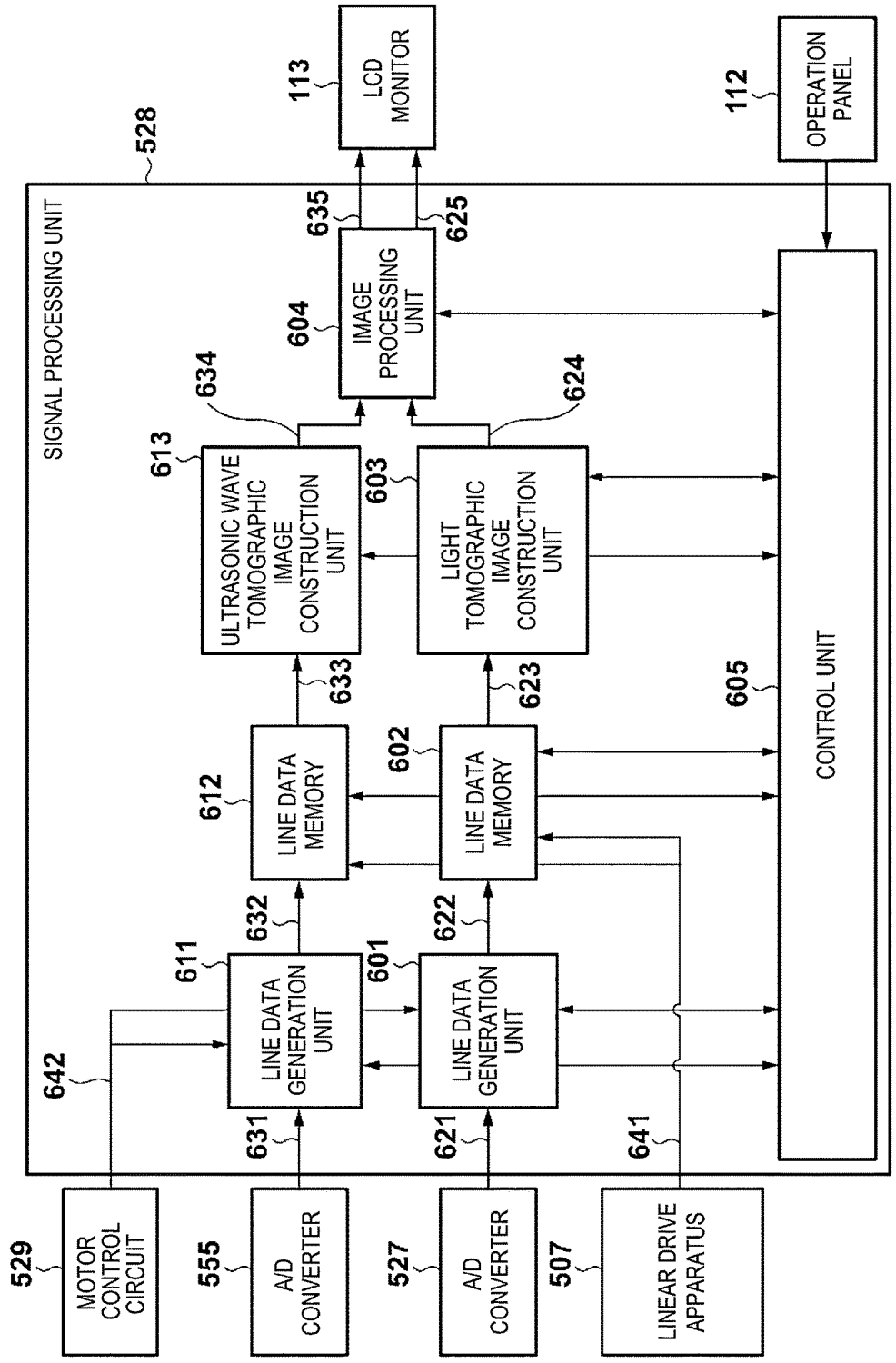
[FIG. 6]

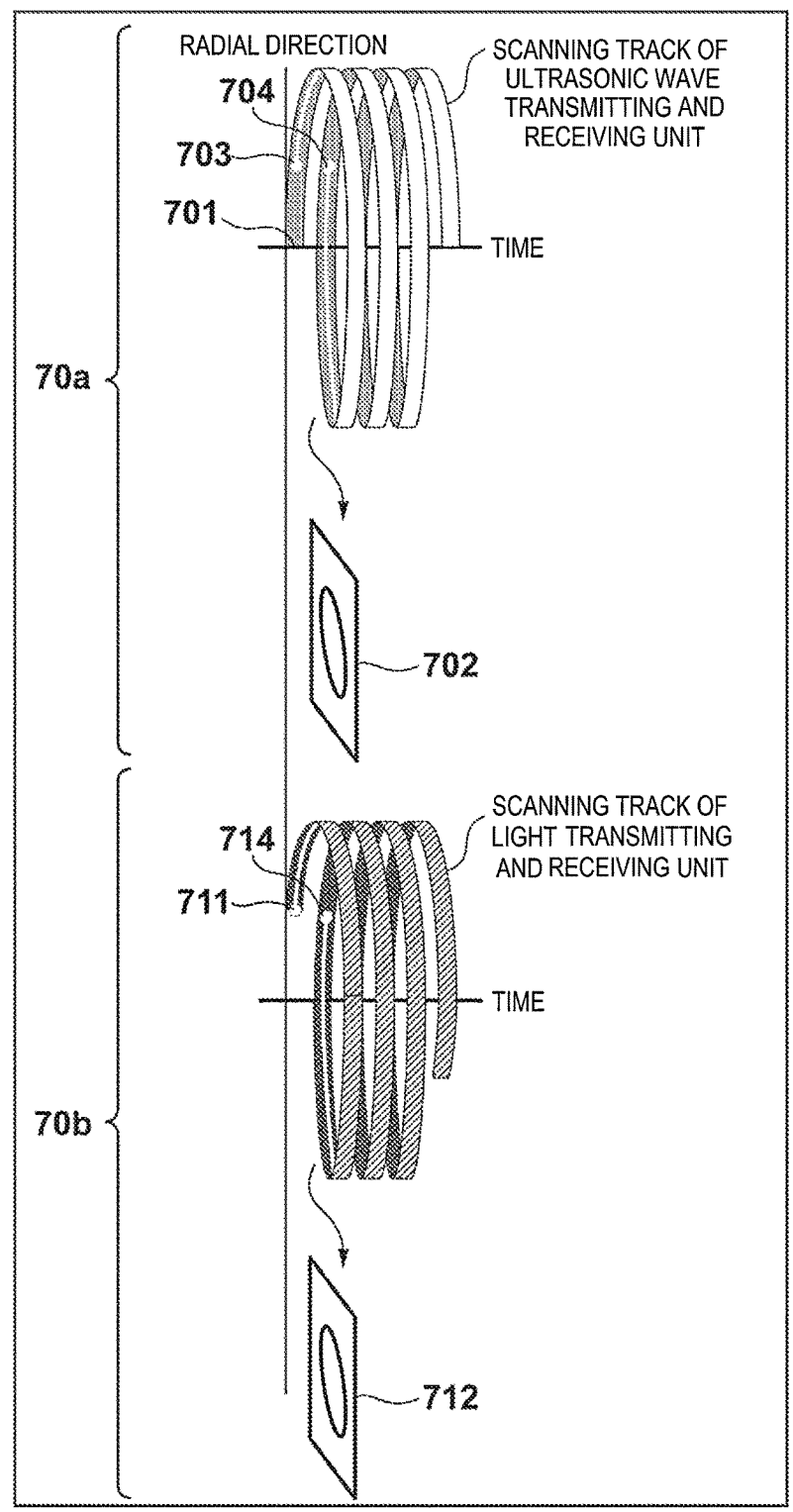
[FIG. 7]

[FIG. 8]
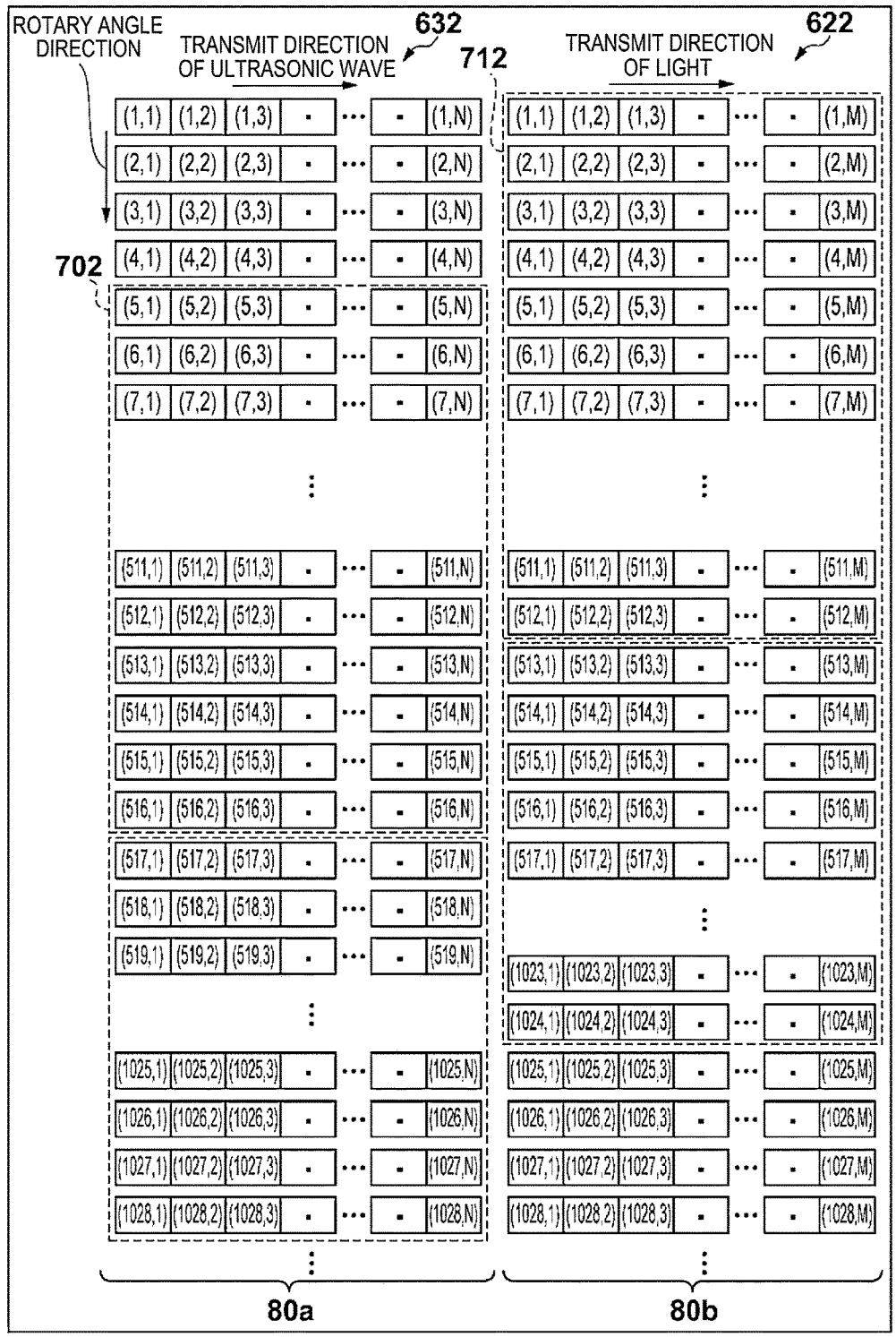

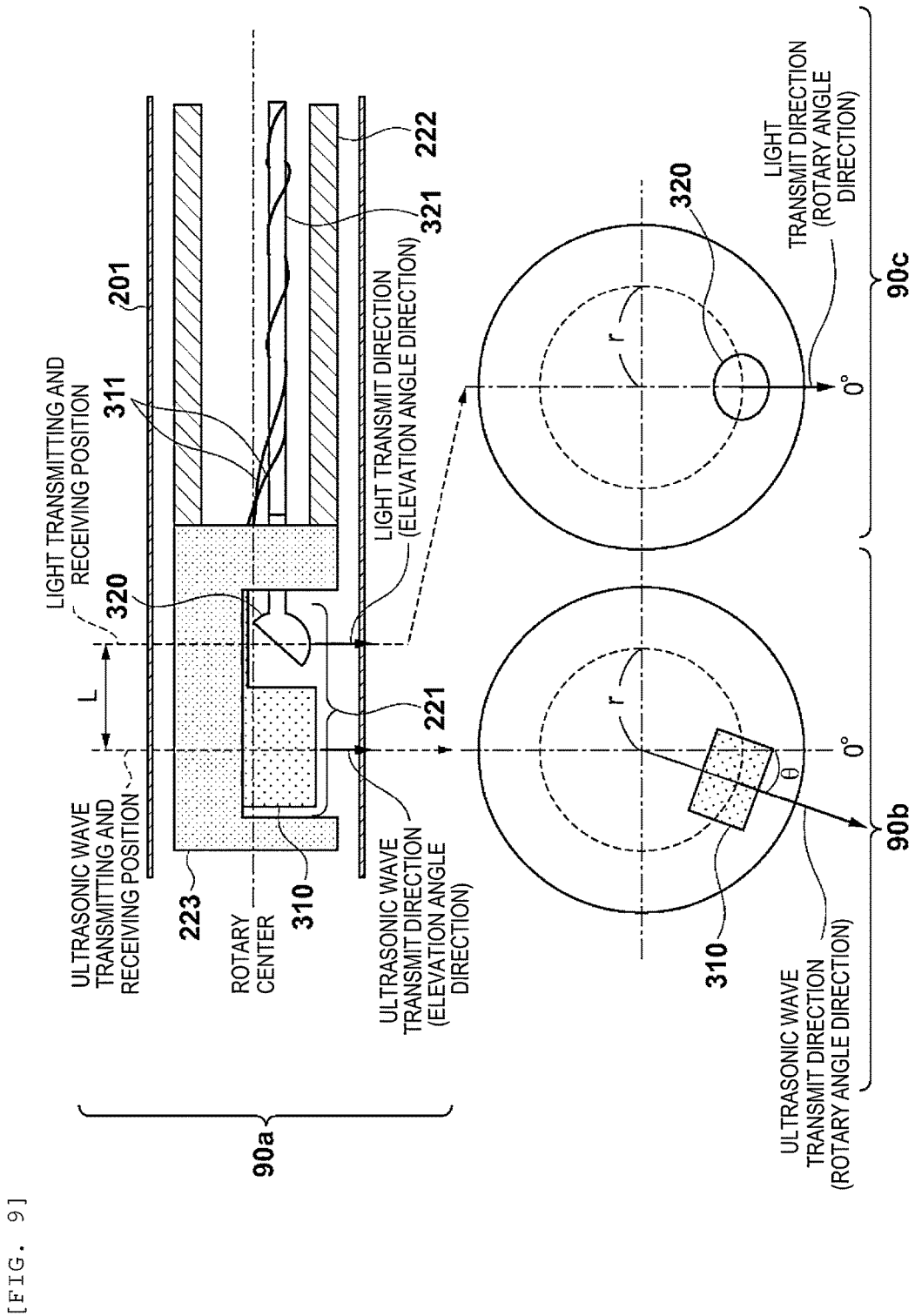
[FIG. 9]

PROBE AND IMAGING APPARATUS FOR DIAGNOSIS

CROSS-REFERENCES TO RELATED APPLICATIONS

This application is a continuation of International Application No. PCT/JP2013/001853 filed on Mar. 19, 2013, and claims priority to Japanese Application No. 2012-069682 filed on Mar. 26, 2012, the entire content of both of which is incorporated herein by reference.

TECHNICAL FIELD

The disclosure here generally relates to a probe and an imaging apparatus for diagnosis.

BACKGROUND INFORMATION

Imaging apparatuses for diagnosis have been widely used to perform diagnoses of arteriosclerosis, preoperative diagnoses during intra-vascular treatment using a high-performance catheter such as a balloon catheter or a stent, and checking postoperative results.

The imaging apparatus for diagnosis includes an intra-vascular ultra sound diagnostic apparatus (IVUS) and an optical coherence tomography (OCT) and the like, each of which has characteristics different from each other.

Recently, there has been proposed an imaging apparatus for diagnosis in which the function of the IVUS and the function of the OCT are combined (for example, refer to Japanese Patent Application Publication No. 11-56752 and Japanese Patent Application Publication No. 2010-508973). According to such an imaging apparatus for diagnosis, it is possible to generate a tomographic image taking advantage of the IVUS which can measure up to a high depth region and an advantage of the OCT which can measure an area in high resolution.

SUMMARY

However, generally in an imaging apparatus for diagnosis, a tomographic image is generated by transmitting and receiving ultrasonic waves or light in a transmitting and receiving unit while a probe unit performs a rotary operation and an axial-direction operation inside a blood vessel. Accordingly, when a transmitting and receiving unit for IVUS and a transmitting and receiving unit for OCT are arranged inside a probe as disclosed in Japanese Patent Application Publication No. 11-56752 and Japanese Patent Application Publication No. 2010-508973, a deviation occurs in scanning positions of an ultrasonic wave and light inside a blood vessel. This is because transmitting and receiving positions of the transmitting and receiving unit for IVUS and the transmitting and receiving unit for OCT cannot be completely the same, since each of the transmitting and receiving unit for IVUS and the transmitting and receiving unit for OCT has a certain size and both need to be arranged so as to be misaligned in a radial direction or an axial direction.

Meanwhile, properties of plaque and the like inside a blood vessel can be effectively observed by using a tomographic image which is generated through the IVUS and a tomographic image which is generated through the OCT. Therefore, when there is any deviation in the scanning position, there is a possibility that the effective observation may not be performed.

For this reason, in such an imaging apparatus for diagnosis described above, it is desirable to match the scanning position inside a blood vessel which is subject to the scanning by the transmitting and receiving unit for IVUS and the scanning position inside the blood vessel which is subject to the scanning by the transmitting and receiving unit for OCT with each other so as to be able to observe completely the same position.

The probe disclosed here has been made taking the aforementioned problems into consideration, and aims to be able to observe the same position in an imaging apparatus for diagnosis in which a transmitting and receiving unit which can transceive an ultrasonic wave and a transmitting and receiving unit which can transceive light are used so as to be able to generate each tomographic image.

The probe includes a transmitting and receiving unit in which an ultrasonic wave transmitting and receiving unit for transmitting and receiving an ultrasonic wave and a light transmitting and receiving unit for transmitting and receiving light are arranged. An ultrasonic wave and light are transmitted while the transmitting and receiving unit rotates. A reflected wave and reflected light can be transferred to an imaging apparatus for diagnosis which uses the reflected wave which is received by the ultrasonic wave transmitting and receiving unit from a biological tissue and the reflected light which is received by the light transmitting and receiving unit from a biological tissue to generate an ultrasonic wave tomographic image and a light tomographic image of the biological tissue in an axial direction, while the probe moves inside a body lumen in the axial direction. The ultrasonic wave transmitting and receiving unit and the light transmitting and receiving unit are arranged so as to make an angular difference θ [degrees] between the ultrasonic wave transmitting and receiving unit and the light transmitting and receiving unit in an azimuth angle direction be proportional to a distance L [mm] between a position of the ultrasonic wave transmitting and receiving unit in the axial direction and a position of the light transmitting and receiving unit in the axial direction and a rotary velocity ω [r/s] of the transmitting and receiving unit, and be inversely proportional to a movement velocity V [mm/s] of the transmitting and receiving unit in the axial direction.

It is possible to observe the same position in an imaging apparatus for diagnosis in which a transmitting and receiving unit which can transceive an ultrasonic wave and a transmitting and receiving unit which can transceive light are used so as to be able to generate each tomographic image.

Other characteristics and advantages will be obvious in the following description with reference to the accompanying drawings. Regarding the accompanying drawings, the same reference numerals and signs will be applied to the same or the similar configurations.

BRIEF DESCRIPTION OF DRAWINGS

The accompanying drawings are incorporated in this specification, take part in the configuration, and illustrate embodiments of the probe and imaging apparatus, thereby being used to explain the description and the principle of the probe and imaging apparatus.

FIG. 1 is a view illustrating an appearance of a configuration of an imaging apparatus for diagnosis 100 according to an embodiment.

FIG. 2 is a view illustrating an overall configuration and a cross-sectional configuration of the distal portion of a probe unit.

FIG. 3 is a view illustrating a cross-sectional configuration of an imaging core, and an arrangement of an ultrasonic wave transmitting and receiving unit and a light transmitting and receiving unit.

FIG. 4A is a view illustrating scanning positions when an ultrasonic wave transmitting and receiving unit and a light transmitting and receiving unit of an imaging apparatus for diagnosis in the related art are caused to perform a rotary operation and an axial-direction operation.

FIG. 4B is a view illustrating scanning positions when the ultrasonic wave transmitting and receiving unit and the light transmitting and receiving unit of the imaging apparatus for diagnosis 100 are caused to perform the rotary operation and the axial-direction operation.

FIG. 5 is a view illustrating a functional configuration of the imaging apparatus for diagnosis 100.

FIG. 6 is a view illustrating a functional configuration of a signal processing unit.

FIG. 7 is a view for describing a correspondence relationship between a tomographic image generated by the imaging apparatus for diagnosis 100 and the scanning positions of the ultrasonic wave transmitting and receiving unit and the light transmitting and receiving unit.

FIG. 8 is a view for describing a correspondence relationship between line data of an ultrasonic wave signal and a light signal generated by the imaging apparatus for diagnosis 100 and frames.

FIG. 9 is a view illustrating another cross-sectional configuration of the imaging core, and another arrangement of the ultrasonic wave transmitting and receiving unit and the light transmitting and receiving unit.

DETAILED DESCRIPTION

Hereinafter, each embodiment of the probe and imaging apparatus disclosed here will be described in detail with reference to the accompanying drawings.

First Embodiment

1. Configuration of Appearance of Imaging Apparatus for Diagnosis

FIG. 1 is a view illustrating an appearance of a configuration of an imaging apparatus for diagnosis 100 (imaging apparatus for diagnosis provided with function of IVUS and function of OCT) according to an embodiment.

As illustrated in FIG. 1, the imaging apparatus for diagnosis 100 includes a probe unit 101, a scanner & pull-back unit 102 and an operation control apparatus 103. The scanner & pull-back unit 102 and the operation control apparatus 103 are connected to each other through a signal wire 104 so as to be able to transfer various signals.

An imaging core which is directly inserted into a body cavity such as a blood vessel is interpolated into the probe unit 101. The imaging core includes an ultrasonic wave transmitting and receiving unit which transmits an ultrasonic wave based on a pulse signal to the inside of a body cavity and receives a reflected wave from the inside of a body cavity, and a light transmitting and receiving unit which continuously transmits transferred light (measurement light) to the inside of a body cavity and continuously receives a reflected light from the inside of a body cavity. In the imaging apparatus for diagnosis 100, the imaging core is used to measure a state inside a body cavity.

The probe unit 101 is detachably attached to the scanner & pull-back unit 102 which regulates the imaging core interpolated into the probe unit 101 regarding an operation in an axial direction and an operation in a rotary direction inside a body cavity by driving a built-in motor. The scanner & pull-back unit 102 acquires the reflected wave received by the ultrasonic wave transmitting and receiving unit and the reflected light received by the light transmitting and receiving unit, thereby performing transmission to the operation control apparatus 103.

The operation control apparatus 103 includes a function for inputting various setting values when performing the measurement, and a function for processing data obtained through measurement and displaying it as a tomographic image inside a body cavity.

In the operation control apparatus 103, the reference numeral 111 indicates a main body control unit, which generates ultrasonic wave data based on a reflected wave obtained through the measurement, and processes line data generated based on the ultrasonic wave data, thereby generating an ultrasonic wave tomographic image. The main body control unit 111 generates interference light data by causing reflected light obtained through the measurement and reference light obtained by separating light from a light source to interfere with each other, and processes the line data generated based on the interference light data, thereby generating a light tomographic image.

The reference numeral 111-1 indicates a printer & DVD recorder, which prints a processing result of the main body control unit 111 or stores the same as data. The reference numeral 112 indicates an operation panel, and a user inputs various setting values and instructions via the operation panel 112. The reference numeral 113 indicates an LCD monitor as a display device, which displays tomographic images generated in the main body control unit 111.

2. Overall Configuration of Probe Unit and Cross-Sectional Configuration of Distal Portion of the Probe Unit Subsequently, an overall configuration of the probe unit 101 and a cross-sectional configuration of the distal portion of the probe unit 101 will be described using FIG. 2. As illustrated in FIG. 2, the probe unit 101 is configured to include an elongated catheter sheath 201 which is inserted into a body cavity such as a blood vessel, and a connector unit 202 which is arranged on a hand side of a user to be manipulated by the user without being inserted into a body cavity such as a blood vessel. A guide wire lumen tube 203 configuring a guide wire lumen is provided at a distal end of the catheter sheath 201. That is, The distal end of the catheter sheath 201 includes a tube 203 possessing a guide wire lumen configured to receive a guide wire. The catheter sheath 201 forms a lumen leading from a portion connected to the guide wire lumen tube 203 to a portion connected to the connector unit 202.

Inside a lumen of the catheter sheath 201, an imaging core 220 including a transmitting and receiving unit 221 and a coil-shaped drive shaft 222 is inserted through the catheter sheath 201 throughout substantially the overall length of the catheter sheath 201. In the transmitting and receiving unit 221, the ultrasonic wave transmitting and receiving unit for transmitting and receiving an ultrasonic wave and the light transmitting and receiving unit for transmitting and receiving light are arranged. The drive shaft 222 is internally provided with an electric signal cable and an optical fiber cable and transfers a rotary drive force for rotating the ultrasonic wave transmitting and receiving unit and the light transmitting and receiving unit.

The connector unit 202 includes a sheath connector 202a which is configured to be unified to a proximal end of the catheter sheath 201, and a drive shaft connector 202b which is configured to rotatably fix the drive shaft 222 at a proximal end of the drive shaft 222.

In a boundary portion between the sheath connector 202*a* and the catheter sheath 201, an anti-kink protector 211 is provided. Accordingly, a predetermined rigidity is maintained and bending (kink) due to a rapid change of physical properties can be prevented.

A proximal end of the drive shaft connector 202*b* is detachably attached to the scanner & pull-back unit 102.

Subsequently, a cross-sectional configuration of a distal portion of the probe unit 101 will be described. Inside the lumen of the catheter sheath 201, the imaging core 220 including a housing 223 and the drive shaft 222 is inserted through throughout substantially the overall length of the catheter sheath 201, thereby forming the probe unit 101. In the housing 223, there is provided the transmitting and receiving unit 221 in which the ultrasonic wave transmitting and receiving unit for transmitting and receiving an ultrasonic wave and the light transmitting and receiving unit for transmitting and receiving light are arranged. The drive shaft 222 transfers a rotary drive force for rotating the ultrasonic wave transmitting and receiving unit and the light transmitting and receiving unit.

The transmitting and receiving unit 221 transmits an ultrasonic wave and light toward a tissue inside a body cavity and receives a reflected wave and reflected light from a tissue inside a body cavity.

The drive shaft 222 is in a coil shape, with the electric signal cable and the optical fiber cable (single mode optical fiber cable) provided inside the drive shaft 222.

The housing 223 is a metallic pipe having a short cylindrical shape in which a notch portion is provided in a portion. The housing 223 is formed through carving from metal ingots, metal powder injection molding (MIM) and the like. The housing 223 internally has the ultrasonic wave transmitting and receiving unit and the light transmitting and receiving unit as the transmitting and receiving unit 221, and a proximal side of the transmitting and receiving unit 221 is connected to the drive shaft 222. A short coil-shaped elastic member 231 is provided on a distal side of the transmitting and receiving unit 221.

The elastic member 231 is a stainless steel wire formed to have a coil shape, and the elastic member 231 is disposed on the distal side so as to be prevented from being caught inside the catheter sheath 201 when the imaging core 220 moves back and forth.

The reference numeral 232 indicates a reinforcement coil which is provided for the purpose of preventing a drastic bend of a distal portion of the catheter sheath 201.

The guide wire lumen tube 203 has a lumen for a guide wire into which a guide wire can be inserted. The guide wire lumen tube 203 receives a guide wire which is inserted into a body cavity such as a blood vessel in advance, thereby being used for guiding the catheter sheath 201 to a target lesion through the guide wire.

The drive shaft 222 is configured with a multiplex-multilayer bonding coil and the like made with a metal wire, for example, stainless steel having characteristics of being able to cause the transmitting and receiving unit 221 to perform a rotary operation and an axial operation with respect to the catheter sheath 201, being soft, and favorably transferring rotations.

3. Cross-Sectional Configuration of Imaging Core

Subsequently, a cross-sectional configuration of the imaging core 220 and an arrangement of the ultrasonic wave transmitting and receiving unit and the light transmitting and receiving unit will be described. FIG. 3 is a view illustrating the cross-sectional configuration of the imaging core, and the arrangement of the ultrasonic wave transmitting and receiving unit and the light transmitting and receiving unit.

As illustrated in 30*a* of FIG. 3, the transmitting and receiving unit 221 which is disposed inside the housing 223 includes an ultrasonic wave transmitting and receiving unit 310 and a light transmitting and receiving unit 320. The ultrasonic wave transmitting and receiving unit 310 and the light transmitting and receiving unit 320 are respectively arranged on a rotary center axis (on a dot and dash line in 30*a*) of the drive shaft 222 along the axial direction.

The ultrasonic wave transmitting and receiving unit 310 of the transmitting and receiving unit 221 is arranged on the distal side of the probe unit 101, and the light transmitting and receiving unit 320 is arranged on the proximal side of the probe unit 101. The ultrasonic wave transmitting and receiving unit 310 and the light transmitting and receiving unit 320 are installed in the housing 223 so as to make a distance L (distance gap) between an ultrasonic wave transmitting and receiving position of the ultrasonic wave transmitting and receiving unit 310 and a light transmitting and receiving position of the light transmitting and receiving unit 320.

The ultrasonic wave transmitting and receiving unit 310 and the light transmitting and receiving unit 320 are installed in the housing 223 so as to make an ultrasonic wave transmit direction (elevation angle direction) of the ultrasonic wave transmitting and receiving unit 310 and a light transmit direction (elevation angle direction) of the light transmitting and receiving unit 320 respectively and substantially 90° with respect to the axial direction of the drive shaft 222. It is desirable for each transmit direction to be slightly misaligned from 90° so as not to receive a reflection of the catheter sheath 201 on the internal surface of a lumen.

Inside the drive shaft 222, an electric signal cable 311 which is connected to the ultrasonic wave transmitting and receiving unit 310 and an optical fiber cable 321 which is connected to the light transmitting and receiving unit 320 are disposed. The electric signal cable 311 is wound in a spiral shape with respect to the optical fiber cable 321.

The reference numeral-sign 30*b* in FIG. 3 is a cross-sectional view when cut on a plane which is substantially orthogonal to the rotary center axis in the ultrasonic wave transmitting and receiving position. As illustrated in 30*b* of FIG. 3, when the downward direction of paper is set to zero, the ultrasonic wave transmit direction (rotary angle direction (also referred to as azimuth angle direction)) of the ultrasonic wave transmitting and receiving unit 310 becomes θ.

The reference numeral-sign 30*c* in FIG. 3 is a cross-sectional view when cut on a plane which is substantially orthogonal to the rotary center axis in the light transmitting and receiving position. As illustrated in 30*c* of FIG. 3, when the downward direction of paper is set to zero, the light transmit direction (rotary angle direction) of the light transmitting and receiving unit 320 becomes zero. That is, the ultrasonic wave transmitting and receiving unit 310 and the light transmitting and receiving unit 320 are arranged so as to cause the ultrasonic wave transmit direction (rotary angle direction) of the ultrasonic wave transmitting and receiving unit 310 and the light transmit direction (rotary angle direction) of the light transmitting and receiving unit 320 to be mutually misaligned by θ.

4. Positional Relationship Between Ultrasonic Wave Transmitting and Receiving Unit and Light Transmitting and Receiving Unit A positional relationship between the ultrasonic wave transmitting and receiving unit 310 and the light transmitting and receiving unit 320 will be further described in detail. As described above, the ultrasonic wave transmitting and receiving unit 310 and the light transmitting and receiving unit 320 are arranged so that the distance between the ultrasonic wave transmitting and receiving position and the light transmitting and receiving position on the rotary center axis along the axial direction is L, and are arranged so that an angular difference between the ultrasonic wave transmit direction (rotary angle direction) and the light transmit direction (rotary angle direction) is θ. The ultrasonic wave transmitting and receiving unit 310 and the light transmitting and receiving unit 320 are arranged on the same axis (on rotary center axis) in order to match the image center of the ultrasonic wave tomographic image and the image center of the light tomographic image which are to be constructed.

Here, the distance L and the angular difference θ have the following relationship in order to match a scanning position by the ultrasonic wave transmitting and receiving unit 310 and a scanning position by the light transmitting and receiving unit 320, when a pullback velocity (movement velocity in axial direction) is $V_{PB}$ [mm/s] and a rotary velocity is ω [r/s] in the scanner & pull-back unit 102 of the imaging apparatus for diagnosis 100 of the present embodiment.

$$L \text{ [mm]} = V_{PB} \text{ [mm/s]}/\omega\text{[r/s]} \times \theta\text{[degrees]}/360 \text{ [degrees]} \quad \text{(Expression 1)}$$

Here, as an example, appropriate values of the distance L and the angular difference θ will be examined below when the pullback velocity $V_{PB}$ is 20 [mm/s] and the rotary velocity ω is 30 [r/s] (1,800 [rpm]) of the scanner & pull-back unit 102.

(1) When Considering Simultaneity

The scanning position by the ultrasonic wave transmitting and receiving unit 310 and the scanning position by the light transmitting and receiving unit 320 can match each other by satisfying Expression 1 above. However, it is not desirable for a scanning timing by the ultrasonic wave transmitting and receiving unit 310 and a scanning timing by the light transmitting and receiving unit 320 to be far apart from each other. This is because when a deviation (differential time) between the scanning timings is significant, the measurement subject may change during the measurement.

Therefore, in the imaging apparatus for diagnosis 100 of the present embodiment, the deviation (differential time) between the scanning timing by the ultrasonic wave transmitting and receiving unit 310 and the scanning timing by the light transmitting and receiving unit 320 with respect to the same scanning position is caused to be less than 1 frame, thereby being configured to enhance the simultaneity of both. In other words, the imaging apparatus for diagnosis 100 of the present embodiment is configured to be θ<360° (that is, to be L [mm]<$V_{PB}$ [mm/s]/ω [r/s]).

(2) When Considering Pulsation

When generating a tomographic image inside a blood vessel, there is a need to consider influence of a pulsation, and it is necessary to suppress changes inside a blood vessel due to a pulsation during the differential time between the scanning timing by the ultrasonic wave transmitting and receiving unit 310 and the scanning timing by the light transmitting and receiving unit 320 with respect to the same scanning position as much as possible. Generally, when the deviation (differential time) between the scanning timings is suppressed to be equal to or less than 10 msec, the changes inside a blood vessel due to a pulsation can be ignored (when equal to or less than 10 msec, the ultrasonic wave transmitting and receiving unit 310 and the light transmitting and receiving unit 320 can be considered as performing the scanning at substantially the same timing).

Based on the facts above, in the imaging apparatus for diagnosis 100 of the present embodiment, the deviation (differential time) between the scanning timing by the ultrasonic wave transmitting and receiving unit 310 and the scanning timing by the light transmitting and receiving unit 320 with respect to the same scanning position is suppressed to be equal to or less than 10 msec, and is thereby configured to enhance the simultaneity of both with respect to a pulsation. In other words, the imaging apparatus for diagnosis 100 of the present embodiment is configured to be θ<108° (=10 [msec]/33.3 [msec/r]×360 [degrees]).

(3) When Considering Size of Transmitting and Receiving Unit

The probe unit 101 is directly inserted into a body cavity such as a blood vessel so that there is a need to suppress a length of the transmitting and receiving unit 221 in the axial direction to be less than 600 [μm], and desirably to be approximately 500 [μm], from a viewpoint of low aggressiveness and in consideration of insertion into a small diameter blood vessel. When considering the manufacturable minimum size of the ultrasonic wave transmitting and receiving unit 310 and the light transmitting and receiving unit 320, it is desirably to suppress the distance L to be equal to or less than 150 [μm].

Based on the facts above, the imaging apparatus for diagnosis 100 of the present embodiment is configured to be θ≤90° (=150 [μm]/20 [mm/s]/30 [r/s]×360 [degrees]).

5. Description for Scanning Position

On account of the above-described positional relationship between the ultrasonic wave transmitting and receiving unit 310 and the light transmitting and receiving unit 320, in the imaging apparatus for diagnosis 100 of the present embodiment, it is possible to perform the scanning of the same scanning position. Hereinafter, using FIGS. 4A and 4B, a relationship between the scanning position of the ultrasonic wave transmitting and receiving unit 310 and the scanning position of the light transmitting and receiving unit 320 will be described.

For comparison, FIG. 4A illustrates a relationship of scanning positions when an ultrasonic wave transmitting and receiving unit and a light transmitting and receiving unit of an imaging apparatus for diagnosis in the related art are caused to perform the rotary operation and the axial-direction operation (relationship of scanning positions when distance L and angular difference θ are not defined so as to make ultrasonic wave transmitting and receiving unit and light transmitting and receiving unit perform scanning of same scanning position).

In reference numeral-signs 40a to 40c of FIG. 4A, a horizontal axis indicates positional coordinates of a body cavity such as a blood vessel in the axial direction, and a vertical axis indicates positional coordinates of a body cavity such as a blood vessel in a radial direction, respectively.

The reference numeral-sign 40a indicates a scanning track of the ultrasonic wave transmitting and receiving unit, and the reference numeral-sign 40b indicates a scanning track of the light transmitting and receiving unit, respectively.

The example of FIG. 4A illustrates an arrangement in which the angular difference θ between the ultrasonic wave transmit direction (rotary angle direction) of the ultrasonic wave transmitting and receiving unit and the light transmit direction (rotary angle direction) of the light transmitting and receiving unit is 0°, and the distance L between the ultrasonic wave transmitting and receiving position and the light transmitting and receiving position on the rotary center axis along the axial direction is L1.

In this case, when the transmitting and receiving unit is caused to perform the rotary operation and the axial-direction operation, as illustrated in 40c of FIG. 4A, the scanning track of the ultrasonic wave transmitting and receiving unit and the scanning track of the light transmitting and receiving unit are misaligned from each other (that is, scanning position of ultrasonic wave transmitting and receiving unit and scanning position of light transmitting and receiving unit are not the same).

Meanwhile, FIG. 4B illustrates a relationship of scanning positions when the ultrasonic wave transmitting and receiving unit 310 and the light transmitting and receiving unit 320 are caused to have the relationship of Expression (1) above.

The example in FIG. 4B illustrates an arrangement in which the angular difference θ between the ultrasonic wave transmit direction (rotary angle direction) of the ultrasonic wave transmitting and receiving unit and the light transmit direction (rotary angle direction) of the light transmitting and receiving unit is θ2, and the distance L between the ultrasonic wave transmitting and receiving position and the light transmitting and receiving position on the rotary center axis along the axial direction is L2.

In this case, when the transmitting and receiving unit 221 is caused to perform the rotary operation and the axial-direction operation, as illustrated in 41c of FIG. 4B, the scanning track of the ultrasonic wave transmitting and receiving unit 310 and the scanning track of the light transmitting and receiving unit 320 match each other (that is, scanning position of ultrasonic wave transmitting and receiving unit 310 and scanning position of light transmitting and receiving unit 320 are the same).

6. Functional Configuration of Imaging Apparatus for Diagnosis

Subsequently, a functional configuration of the imaging apparatus for diagnosis 100 will be described. FIG. 5 is a view illustrating a functional configuration of the imaging apparatus for diagnosis 100 in which a function of IVUS and a function of OCT (herein, wavelength sweep-type OCT, for example) are combined. An imaging apparatus for diagnosis in which a function of IVUS and a function of other type of OCT are combined also has a similar functional configuration. The description of such a configuration is not repeated.

(1) Function of IVUS

The imaging core 220 includes the ultrasonic wave transmitting and receiving unit 310 inside the distal end of the imaging core 220. The ultrasonic wave transmitting and receiving unit 310 transmits an ultrasonic wave to a biological tissue based on a pulse wave transmitted from an ultrasonic wave signal transmitting and receiving unit 552, receives a reflected wave (echo) of the transmitted ultrasonic wave, and transmits the reflected wave to the ultrasonic wave signal transmitting and receiving unit 552 as an ultrasonic wave echo via an adaptor 502 and a slip ring 551.

A rotary drive portion side of the slip ring 551 is rotationally driven by a radial scanning motor 505 of a rotary drive apparatus 504. A rotary angle of the radial scanning motor 505 is detected by an encoder unit 506. The scanner & pull-back unit 102 includes a linear drive apparatus 507 and defines the axial-direction operation of the imaging core 220 based on a signal from a signal processing unit 528.

The ultrasonic wave signal transmitting and receiving unit 552 includes a transmit wave circuit and a reception wave circuit (not illustrated). The transmit wave circuit transmits a pulse wave to the ultrasonic wave transmitting and receiving unit 310 inside the imaging core 220 based on a control signal transmitted from the signal processing unit 528.

The reception wave circuit receives an ultrasonic wave signal from the ultrasonic wave transmitting and receiving unit 310 inside the imaging core 220. The received ultrasonic wave signal is input to a wave detector 554 after being amplified by an amplifier 553, thereby performing wave-detecting.

In an A/D converter 555, ultrasonic wave signals output from the wave detector 554 are sampled at as many as 200 points at 30.6 MHz, thereby generating digital data (ultrasonic wave data) of 1 line. The frequency is set to 30.6 MHz herein on a premise that 200 points are to be sampled with respect to the depth of 5 mm when the sound velocity is considered to be 1,530 m/sec. Therefore, the sampling frequency is not particularly limited thereto.

The ultrasonic wave data in a line unit generated in the A/D converter 555 is input to the signal processing unit 528. In the signal processing unit 528, the ultrasonic wave data is converted into a gray scale so as to form the ultrasonic wave tomographic image in each position inside a body cavity such as a blood vessel, thereby outputting the ultrasonic wave tomographic image to the LCD monitor 113 at a predetermined frame rate.

The signal processing unit 528 is connected to a motor control circuit 529, thereby receiving a video synchronization signal of the motor control circuit 529. In the signal processing unit 528, the ultrasonic wave tomographic image is constructed being synchronized with the received video synchronization signal.

The video synchronization signal of the motor control circuit 529 is also transmitted to the rotary drive apparatus 504, and the rotary drive apparatus 504 outputs a drive signal which is synchronized with the video synchronization signal.

(2) Function of Wavelength Sweep-Type OCT

The reference numeral 508 indicates a wavelength swept light source (swept laser), and it is a type of an extended-cavity laser which is configured to have an optical fiber 516 which is coupled with a semiconductor optical amplifier 515 (SOA) in a ring shape, and a polygon scanning filter (508b).

Light output from the SOA 515 proceeds through the optical fiber 516 and is input to the polygon scanning filter 508b. The light is subjected to wavelength selection herein, is amplified in the SOA 515, and lastly, is output from a coupler 514.

In the polygon scanning filter 508b, the wavelength is selected by combining a diffraction grating 512 which disperses light, and a polygon mirror 509. Specifically, rays of light dispersed by the diffraction grating 512 are concentrated on a surface of the polygon mirror 509 by using two lenses (510, 511). Accordingly, only the light having a wavelength which is orthogonal to the polygon mirror 509 returns the same optical path, thereby being output from the polygon scanning filter 508b. In other words, time sweep of a wavelength can be performed by rotating the polygon mirror 509.

In the polygon mirror 509, for example, a 32-hedron mirror is used and the number of rotations is approximately 50,000 rpm. High speed and high output wavelength sweep can be performed through the wavelength sweep method in which the polygon mirror 509 and the diffraction grating 512 are combined.

Light of the wavelength swept light source 508 which is output from the coupler 514 is incident on an end of a first single mode fiber 540, thereby being transmitted to the distal side of the first single mode fiber 540. The first single mode fiber 540 is optically coupled to a second single mode fiber 545 and a third single mode fiber 544 in an photo coupler unit 541 which is between the second single mode fiber 545 and the third single mode fiber 544. Therefore, light incident on the first single mode fiber 540 is divided into three optical paths at the maximum by the photo coupler unit 541, thereby being transmitted.

On a further distal side than the photo coupler unit 541 of the first single mode fiber 540, an optical rotary joint (optical coupling portion) 503 which connects a non-rotary portion (fixing portion) and a rotary portion (rotary drive portion) with each other and transfers light is provided inside the rotary drive apparatus 504.

On a distal side of a fourth single mode fiber 542 inside the optical rotary joint (optical coupling portion) 503, a fifth single mode fiber 543 of the probe unit 101 is freely and detachably connected via the adaptor 502. Accordingly, light from the wavelength swept light source 508 is transferred to the fifth single mode fiber 543 which is inserted through the imaging core 220 to be rotatably driven.

Emission of transferred light is performed while being subjected to the rotary operation and the axial-direction operation from the light transmitting and receiving unit 320 of the imaging core 220 to a biological tissue inside a body lumen. A portion of reflected light scattered in the inside or on a surface of a biological tissue is collected by the light transmitting and receiving unit 320 of the imaging core 220, thereby returning to the first single mode fiber 540 side via an optical path in reverse. The portion of the reflected light moves to the second single mode fiber 545 side by the photo coupler unit 541, and the light is received by the light detector (for example, photo-diode 524) after being emitted from an end of the second single mode fiber 545.

The rotary drive portion side of the optical rotary joint 503 is rotationally driven by the radial scanning motor 505 of the rotary drive apparatus 504. A rotary angle of the radial scanning motor 505 is detected by the encoder unit 506. The scanner & pull-back unit 102 includes the linear drive apparatus 507 and defines the axial-direction operation of the imaging core 220 based on an instruction from the signal processing unit 528.

Meanwhile, an optical path length varying mechanism 532 for fine-adjusting the optical path length of the reference light is provided in a distal end on a side opposite to the photo coupler unit 541 of the third single mode fiber 544.

The optical path length varying mechanism 532 includes optical path length changing means for changing the optical path length corresponding to a fluctuation in a length of each probe unit 101 so as to be able to absorb the fluctuation in the length of each probe unit 101 when the probe unit 101 is replaced and used.

The third single mode fiber 544 and a collimating lens 518 are provided on a one-axis stage 522 which is movable in an optical-axis direction as indicated by the arrow 523, thereby forming the optical path length changing means.

Specifically, the one-axis stage 522 functions as the optical path length changing means having a movable range of the optical path length as wide as the fluctuation in the optical path length of the probe unit 101 can be absorbed when the probe unit 101 is replaced. The one-axis stage 522 also includes a function as adjustment means for adjusting an offset. For example, when the distal end of the probe unit 101 is not in close contact with a surface of a biological tissue, it is possible to set a state of being interfered with the reflected light from the surface position of the biological tissue by minutely changing the optical path length through the one-axis stage.

The optical path length is fine-adjusted in the one-axis stage 522, and light reflected by the mirror 521 via a grating 519 and a lens 520 is mixed with light acquired from the first single mode fiber 540 side in the photo coupler unit 541 which is provided in an intermediate portion of the third single mode fiber 544, and thus, the light is received in the photo-diode 524.

The interference light received in the photo-diode 524 in such a manner is subjected to photoelectric conversion, thereby being input to a demodulator 526 after being amplified by the amplifier 525. In the demodulator 526, demodulation processing in which only the signal portion is extracted from the interfered light is performed, and the output is input to an A/D converter 527 as an interference light signal.

In the A/D converter 527, an interference light signal is sampled, for example, at as many as 2,048 points at 180 MHz, thereby generating digital data (interference light data) of 1 line. The sampling frequency is set to 180 MHz on a premise that approximately 90% of a periodical cycle (12.5 μsec) of the wavelength sweep is extracted as digital data of 2,048 points when a repetition frequency of the wavelength sweep is set to 40 kHz, without being particularly limited thereto.

The interference light data in a line unit generated in the A/D converter 527 is input to the signal processing unit 528. When in a measurement mode, the interference light data is subjected to frequency resolution through fast Fourier transform (FFT) in the signal processing unit 528 so as to generate data in a depth direction (line data). The line data is subjected to coordinate-conversion to construct a light tomographic image in each position inside a body cavity such as a blood vessel, thereby being output to the LCD monitor 113 at a predetermined frame rate.

The signal processing unit 528 is further connected to an optical path length adjustment means control device 530. The signal processing unit 528 controls a position of the one-axis stage 522 via the optical path length adjustment means control device 530.

7. Functional Configuration of Signal Processing Unit

Subsequently, in the signal processing unit 528 of the imaging apparatus for diagnosis 100, a functional configuration of the signal processing unit 528 for constructing a tomographic image will be described with reference to FIG. 6. The construction processing described below may be realized using an exclusive hardware, or may be realized using a software (through execution of program by computer).

FIG. 6 is a view illustrating a functional configuration and functional blocks related thereto for realizing the construction processing in the signal processing unit 528 of the imaging apparatus for diagnosis 100.

As illustrated in FIG. 6, the interference light data 621 generated in the A/D converter 527 is processed so as to have the number of lines per one rotation in the radial scanning become 512 in a line data generation portion 601 inside the signal processing unit 528, using a signal of the encoder unit 506 of the radial scanning motor 505 which is output from the motor control circuit 529.

Herein, as an example, the light tomographic image is constructed with 512 lines. However, the construction is not limited to the number of the lines.

Line data 622 which is output from the line data generation portion 601 is stored in a line data memory 602 for one rotation of the radial scanning based on an instruction from a control unit 605. In this case, in the control unit 605, pulse signals 641 which are output from a movement amount detector of the linear drive apparatus 507 are counted so as to be stored while the count value at the time the line data 622 is individually generated corresponds to the counted pulse signals 641 when the line data 622 is stored in the line data memory 602.

Stored line data 623 corresponding to the count value is subjected to Rθ conversion after performing various processing (line addition-averaging processing, filtering processing and the like) in a light tomographic image construction unit 603 based on an instruction from the control unit 605, thereby being sequentially output as the light tomographic image 624.

In an image processing unit 604, after performing the image processing to be displayed on the LCD monitor 113, the line data 623 is output to the LCD monitor 113 as the light tomographic image 625.

Similarly, ultrasonic wave data 631 generated in the A/D converter 555 is processed so as to have the number of lines per one rotation in the radial scanning become 512 in a line data generating unit 611 inside the signal processing unit 528, using a signal of the encoder unit 506 of the radial scanning motor 505 which is output from the motor control circuit 529.

Line data 632 which is output from the line data generating unit 611 is stored in a line data memory 612 for one rotation of the radial scanning based on an instruction from the control unit 605. In this case, in the control unit 605, pulse signals 641 which are output from the movement amount detector of the linear drive apparatus 507 are counted so as to be stored while the count value at the time the line data 632 is individually generated corresponds to the counted pulse signals 641 when the line data 632 is stored in the line data memory 612.

The count value to be stored while corresponding to the line data 632 which is stored for one rotation of the radial scanning is misaligned with the count value to be stored while corresponding to the line data 622 which is stored for one rotation of the radial scanning by the count value corresponding to the angular difference θ between the ultrasonic wave transmit direction (rotary angle direction) and the light transmit direction (rotary angle direction). Description will be given in detail with reference to FIGS. 7 and 8.

FIG. 7 is a view for describing a correspondence relationship between the ultrasonic wave tomographic image and the light tomographic image generated by the imaging apparatus for diagnosis 100, and the scanning positions of the ultrasonic wave transmitting and receiving unit 310 and the light transmitting and receiving unit 320. FIG. 8 is a view for describing a correspondence relationship between the line data 632 of the ultrasonic wave data and the line data 622 of the interference light data generated by the imaging apparatus for diagnosis 100, and frames.

In the reference numeral-signs 70a and 70b of FIG. 7, the horizontal axis indicates time, and the vertical axis indicates positional coordinates of a body cavity such as a blood vessel in a radial direction, respectively. The reference numeral-sign 70a indicates the scanning track of the ultrasonic wave transmitting and receiving unit 310, and the reference numeral-sign 70b indicates a scanning track of the light transmitting and receiving unit 320, respectively.

As described above, since the ultrasonic wave transmit direction (rotary angle direction) and the light transmit direction (rotary angle direction) have an angular difference θ, when the radial scanning is started simultaneously, the scanning position of the ultrasonic wave transmitting and receiving unit 310 and the scanning position of the light transmitting and receiving unit 320 become different from each other each time (for example, at the time the radial scanning starts, the ultrasonic wave transmitting and receiving unit 310 performs the scanning of the scanning position indicated by the reference numeral 701, and to the contrary, the light transmitting and receiving unit 320 performs scanning of the scanning position indicated by the reference numeral 711).

Therefore, when the line data 632 for one frame of the ultrasonic wave tomographic image and the line data 622 for one frame of the light tomographic image are configured to be taken at the same timing, each of the tomographic images are constructed using the line data of the scanning positions which are different from each other.

Accordingly, based on the differential time as much as the angular difference between the ultrasonic wave transmit direction (rotary angle direction) and the light transmit direction (rotary angle direction), the imaging apparatus for diagnosis 100 of the present embodiment is configured to take the line data for one rotation of the radial scanning.

For example, an ultrasonic wave tomographic image 702 is an ultrasonic wave tomographic image which is constructed by storing the line data acquired at the timing 703 as the first line data for one rotation of the radial scanning, and storing the line data acquired at the timing 704 as the 512th line data for one rotation of the radial scanning.

Meanwhile, a light tomographic image 712 is a light tomographic image which is constructed by storing the line data acquired at the timing 711 as the first line data for one rotation of the radial scanning, and storing the line data acquired at the timing 714 as the 512th line data for one rotation of the radial scanning.

The reference numeral-sign 80a of FIG. 8 is a view illustrating an example of the line data 632 stored in the line data memory 612 in a manner described above, and the reference numeral-sign 80b of FIG. 8 is a view illustrating an example of the line data 622 stored in the line data memory 602.

As learned from the comparison between 80a in FIGS. 8 and 80b in FIG. 8, the line data 632 for one rotation of the radial scanning and the line data 622 for one rotation of the radial scanning are stored in the line data memory 612 while being misaligned from each other by angular difference θ.

Description returns to FIG. 6. Stored line data 633 corresponding to the count value is subjected to Rθ conversion after performing various processing (line addition-averaging processing, filtering processing and the like) in a ultrasonic wave tomographic image construction unit 613 based on an instruction from the control unit 605, thereby being sequentially output as the ultrasonic wave tomographic image 634.

In the image processing unit 604, after performing the image processing to be displayed on the LCD monitor 113, the line data 633 is output to the LCD monitor 113 as the ultrasonic wave tomographic image 635.

As it is obvious from the description above, in the imaging apparatus for diagnosis 100 of the present embodiment, when being arranged on the rotary center axis along the axial direction, the ultrasonic wave transmitting and receiving unit 310 and the light transmitting and receiving unit 320 are arranged to correspond to the pullback velocity and the rotary velocity in the scanner & pull-back unit.

The distance between the ultrasonic wave transmitting and receiving unit 310 and the light transmitting and receiving unit 320 and the angular difference in the rotary angle direction are configured to be determined in consideration of the simultaneity in measurement and influence of a pulsation therebetween and the size of the transmitting and receiving unit.

The line data used for constructing one frame of the ultrasonic wave tomographic image and the line data used for constructing one frame of the light tomographic image are configured to be determined in accordance with the angular difference between the ultrasonic wave transmitting and receiving unit 310 and the light transmitting and receiving unit 320 in the rotary angle direction.

As a result, it is possible to observe the same position in an imaging apparatus for diagnosis in which the ultrasonic wave transmitting and receiving unit and the light transmitting and receiving unit are used to be able to respectively generate the tomographic images.

Second Embodiment

In the first embodiment, the ultrasonic wave transmitting and receiving unit 310 and the light transmitting and receiving unit 320 are configured to be arranged on the rotary center axis along the axial direction. However, the probe unit disclosed here is not limited to the above configuration. The ultrasonic wave transmitting and receiving unit 310 and the light transmitting and receiving unit 320 may be configured to be misaligned from the rotary center axis. This is because each of the image centers can be adjusted through the image processing when generating the ultrasonic wave image and when generating the light tomographic image. Therefore, the ultrasonic wave transmitting and receiving unit 310 and the light transmitting and receiving unit 320 are not necessarily arranged on the rotary center axis.

FIG. 9 is a view illustrating another cross-sectional configuration of the imaging core, and another arrangement of the ultrasonic wave transmitting and receiving unit and the light transmitting and receiving unit in the imaging apparatus for diagnosis of the present embodiment. Herein, the description will be given focusing on the dissimilarity with FIG. 3.

As illustrated in FIG. 9, in the imaging apparatus for diagnosis of the present embodiment, the ultrasonic wave transmitting and receiving unit 310 and the light transmitting and receiving unit 320 are arranged in positions apart from the rotary center axis by distance r, and arranged to cause the angular difference between the ultrasonic wave transmit direction (rotary angle direction) and the light transmit direction (rotary angle direction) to be θ.

In this manner, the ultrasonic wave transmitting and receiving unit and the light transmitting and receiving unit can observe the same position by being configured to be respectively arranged in positions at equivalent distances from the rotary center axis along the axial direction, similar to the first embodiment.

Third Embodiment

In the first embodiment, the ultrasonic wave transmitting and receiving unit 310 is arranged on the distal side and the light transmitting and receiving unit 320 is arranged on the proximal side in the configuration. However, the probe unit disclosed here is not limited in this particular configuration. The light transmitting and receiving unit 320 may be arranged on the distal side of the probe unit 101 and the ultrasonic wave transmitting and receiving unit 310 may be arranged on the proximal side of the probe unit 101 in the configuration.

In the first embodiment, there is no particular mention regarding an aspect of displaying the constructed ultrasonic wave tomographic image and light tomographic image. However, the ultrasonic wave tomographic image and the light tomographic image may be configured to display the tomographic images which respectively correspond to the positions inside a body cavity such as a blood vessel in the axial direction in parallel, or may be configured to display the same to overlap with each other so as to match the image centers.

The detailed description above describes embodiments of a probe unit and imaging apparatus representing examples of the probe unit and imaging apparatus of the present invention. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A probe comprising:
a transmitting and receiving unit in which an ultrasonic wave transmitting and receiving unit for transmitting and receiving an ultrasonic wave and a light transmitting and receiving unit for transmitting and receiving light are arranged, the ultrasonic wave transmitting and receiving unit being spaced from the light transmitting and receiving unit in an axial direction by an axial distance L [mm],
wherein an ultrasonic wave and light are transmitted while the transmitting and receiving unit rotates,
wherein, during operation of the probe, a reflected wave and a reflected light are transmitted to an operation control apparatus of an imaging apparatus for diagnosis which uses the reflected wave received by the ultrasonic wave transmitting and receiving unit from a biological tissue and the reflected light received by the light transmitting and receiving unit from a biological tissue to generate an ultrasonic wave tomographic image and a light tomographic image of the biological tissue in an axial direction, while the probe moves inside a body lumen in the axial direction,
the ultrasonic wave transmitting and receiving unit and the light transmitting and receiving unit being arranged relative to one another such that an angular difference θ [degrees] other than 0° exists between the ultrasonic wave transmitting and receiving unit and the light transmitting and receiving unit in an azimuth angle direction,
a rotary drive connected to the transmitting and receiving unit to rotate the transmitting and receiving unit at a rotary velocity ω [r/s],
a linear drive connected to the transmitting and receiving unit to move the transmitting and receiving unit in the axial direction at a movement velocity V [mm/s],
the rotary drive being controlled so that the angular difference θ [degrees] is directly proportional to the distance L [mm] in the axial direction and to the rotary velocity ω [r/s] of the transmitting and receiving unit, and
the rotary drive and the linear drive being controlled so that the angular difference θ [degrees] between the ultrasonic wave transmitting and receiving unit and the light transmitting and receiving unit in the azimuth angle direction is inversely proportional to the movement velocity V [mm/s] of the transmitting and receiving unit in the axial direction.

2. The probe according to claim 1, wherein the ultrasonic wave transmitting and receiving unit and the light transmitting and receiving unit are arranged such that the distance L [mm] between the position of the ultrasonic wave transmitting and receiving unit in the axial direction and the position of the light transmitting and receiving unit in the axial direction, and the angular difference θ [degrees] between the azimuth angle directions of the ultrasonic wave transmitting and receiving unit and the light transmitting and receiving unit satisfy a relationship of L=V/ω×θ/360 when having the rotary velocity ω [r/s] of the transmitting and receiving unit and the movement velocity V [mm/s] of the transmitting and receiving unit in the axial direction.

3. The probe according to claim 2, wherein the angular difference θ is smaller than 360°.

4. The probe according to claim 3, wherein a differential time between a timing the ultrasonic wave transmitting and receiving unit performs scanning of a position inside the body lumen and a timing the light transmitting and receiving unit performs scanning of the same position inside the body lumen is equal to or smaller than 10 msec.

5. The probe according to claim 4, wherein the distance L [mm] is equal to or shorter than 150 [μm].

6. The probe according to claim 1, wherein an elevation angle of a transmit direction of the ultrasonic wave from the ultrasonic wave transmitting and receiving unit and a transmit direction of the light from the light transmitting and receiving unit with respect to the axial direction is substantially 90°.

7. An imaging apparatus for diagnosis which generates an ultrasonic wave tomographic image and a light tomographic image using the reflected wave and the reflected light which are transmitted from the probe according to claim 1,
wherein each frame of the ultrasonic wave tomographic image and the light tomographic image is constructed using line data which is generated based on the reflected wave and the reflected light acquired when the ultrasonic wave transmitting and receiving unit and the light transmitting and receiving unit respectively perform scanning of an identical scanning position.

8. A probe comprising:
a rotatable transmitting and receiving unit in which an ultrasonic wave transmitting and receiving unit for transmitting and receiving an ultrasonic wave and a light transmitting and receiving unit for transmitting and receiving light are arranged,
a rotary drive connected to the transmitting and receiving unit to rotate the transmitting and receiving unit at a rotary velocity ω [r/s],
a linear drive connected to the transmitting and receiving unit to move the transmitting and receiving unit in the axial direction at a movement velocity V [mm/s],
the ultrasonic wave transmitting and receiving unit being configured to emit an ultrasonic wave while the transmitting and receiving unit rotates and moves in the axial direction, and the light transmitting and receiving unit being configured to emit light while the transmitting and receiving unit rotates and moves in the axial direction,
the ultrasonic wave transmitting and receiving unit and the light transmitting and receiving unit being arranged relative to one another such that an angular difference θ [degrees] other than 0° exists between the ultrasonic wave transmitting and receiving unit and the light transmitting and receiving unit in an azimuth angel direction,
a reflected wave and a reflected light being transmitted to an operation control apparatus of an imaging apparatus for diagnosis which uses the reflected wave received by the ultrasonic wave transmitting and receiving unit from a biological tissue and the reflected light received by the light transmitting and receiving unit from the biological tissue to generate an ultrasonic wave tomographic image and a light tomographic image of the biological tissue in an axial direction, while the probe moves inside a body lumen in the axial direction, and the ultrasonic wave transmitting and receiving unit and the light transmitting and receiving unit being arranged along the axial direction, and the rotary drive and the linear drive being controlled so that a value of V/ω× θ/360 is smaller than 600 [μm].

9. The probe according to claim 1, wherein an angle between the axial direction and an ultrasonic wave transmit direction is substantially equivalent to an angle between the axial direction and a light transmit direction.

10. The probe according to claim 8, wherein an angle between the axial direction and an ultrasonic wave transmit direction is substantially equivalent to an angle between the axial direction and a light transmit direction.

11. The probe according to claim 8, wherein the angular difference θ is smaller than 360°, and the distance L [mm] is equal to or shorter than 150 [μm].

12. The probe according to claim 8, wherein a differential time between a timing the ultrasonic wave transmitting and receiving unit performs scanning of a position inside the body lumen and a timing the light transmitting and receiving unit performs scanning of the same position inside the body lumen is equal to or smaller than 10 msec.

13. The probe according to claim 8, wherein an elevation angle of a transmit direction of the ultrasonic wave from the ultrasonic wave transmitting and receiving unit and a transmit direction of the light from the light transmitting and receiving unit with respect to the axial direction is substantially 90°.

14. An imaging apparatus for diagnosis comprising:
a probe unit including a rotatable transmitting and receiving unit;
the transmitting and receiving unit including i) an ultrasonic wave transmitting and receiving unit that performs ultrasonic wave transmission and reception, and ii) an optical transmitting and receiving unit that performs light transmission and reception;
the ultrasonic wave transmitting and receiving unit being spaced from the light transmitting and receiving unit in an axial direction by an axial distance L [mm];
a rotary drive connected to the transmitting and receiving unit to rotate the transmitting and receiving unit at a rotary velocity ω [r/s];
a linear drive connected to the transmitting and receiving unit to move the transmitting and receiving unit in the axial direction at a movement velocity V [mm/s];
an operation control apparatus;
the ultrasonic wave transmitting and receiving unit being configured to emit an ultrasonic wave while the transmitting and receiving unit rotates and moves in the axial direction, and the light transmitting and receiving unit being configured to emit light while the transmitting and receiving unit rotates and moves in the axial direction;
a reflected wave and a reflected light being transmitted to the operation control apparatus, the operation control apparatus using the reflected wave received by the ultrasonic wave transmitting and receiving unit from a biological tissue to generate an ultrasonic wave tomographic image, and the reflected light received by the light transmitting and receiving unit from the biological tissue to generate a light tomographic image of the biological tissue in an axial direction;

the ultrasonic wave transmitting and receiving unit and the light transmitting and receiving unit being arranged relative to one another such that an angular difference θ [degrees] other than 0° exists between the ultrasonic wave transmitting and receiving unit and the light transmitting and receiving unit in an azimuth angle direction, the rotary drive being configured to rotate the transmitting and receiving unit so that the angular difference θ [degrees] is directly proportional to i) the distance L [mm] in the axial direction and ii) the rotary velocity ω [r/s] of the transmitting and receiving unit; and the linear drive being configured to move the transmitting and receiving unit in the axial direction so that the angular difference θ [degrees] is inversely proportional to the movement velocity V [mm/s] of the transmitting and receiving unit in the axial direction.

15. The tomographic image generation device according to claim 14, wherein a value of V/ω×θ/360 is smaller than 600 [μm].

16. A method comprising:

introducing a probe unit of an imaging apparatus into a blood vessel, the probe unit comprising: a transmitting and receiving unit comprised of an ultrasonic wave transmitting and receiving unit that performs ultrasonic wave transmission and reception; an optical transmitting and receiving unit that performs light transmission and reception; the ultrasonic wave transmitting and receiving unit being spaced apart in an axial direction from the light transmitting and receiving unit by an axial distance L [mm]; the ultrasonic wave transmitting and receiving unit being rotationally offset from the light transmitting and receiving unit at an angular difference θ [degrees] in an azimuth angle direction;

rotating the transmitting and receiving unit at a rotary velocity ω [r/s] and moving the transmitting and receiving unit at a movement velocity V [mm/s] in the axial direction while also transmitting both the ultrasonic wave and the light toward biological tissue in the blood vessel;

the ultrasonic wave transmitting and receiving unit receiving the ultrasonic wave reflected from the biological tissue in the blood vessel, and the light transmitting and receiving unit receiving the light reflected from the biological tissue in the blood vessel;

the reflected ultrasonic wave being used to generate an ultrasonic wave tomographic image in the axial direction, and the reflected light being used to generate a light tomographic image of the biological tissue in the axial direction; and a value of V/ω×θ/360 is smaller than 600 [μm].

17. The method according to claim 16, wherein L=V/ω× θ/360.

* * * * *